(12) United States Patent
Wada (10) Patent No.: US 10,632,028 B2
(45) Date of Patent: Apr. 28, 2020

(54) COMPOSITE SHEET MATERIAL, DISPOSABLE WEARING ARTICLE USING THE SAME, AND PRODUCTION METHOD AND PRODUCTION APPARATUS FOR COMPOSITE SHEET MATERIAL

(71) Applicant: ZUIKO CORPORATION, Osaka (JP)

(72) Inventor: Takao Wada, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 812 days.

(21) Appl. No.: 14/443,030

(22) PCT Filed: Nov. 15, 2013

(86) PCT No.: PCT/JP2013/080897
§ 371 (c)(1),
(2) Date: May 14, 2015

(87) PCT Pub. No.: WO2014/084066
PCT Pub. Date: Jun. 5, 2014

(65) Prior Publication Data
US 2015/0290050 A1 Oct. 15, 2015

(30) Foreign Application Priority Data
Nov. 30, 2012 (JP) .................................. 2012-262705

(51) Int. Cl.
*A61F 13/511* (2006.01)
*A61F 13/512* (2006.01)
(Continued)

(52) U.S. Cl.
CPC .. *A61F 13/51104* (2013.01); *A61F 13/15707* (2013.01); *A61F 13/15739* (2013.01);
(Continued)

(58) Field of Classification Search
CPC .......... A61F 13/15707; A61F 13/15739; A61F 13/511; A61F 13/51104; A61F 13/5116;
(Continued)

(56) References Cited

U.S. PATENT DOCUMENTS 3,370,520 A * 2/1968 Mauch .................. A47C 7/021
428/178
3,468,311 A * 9/1969 Gallagher ............. A61F 5/4401
428/131
(Continued)

FOREIGN PATENT DOCUMENTS

CN         101842233 A    9/2010
JP         2004174234 A   6/2004
(Continued)

OTHER PUBLICATIONS

International Search Report and Written Opinion in corresponding PCT/JP2013/080897 dated Feb. 18, 2014.
(Continued)

*Primary Examiner* — Kathryn E Ditmer
(74) *Attorney, Agent, or Firm* — Marshall, Gerstein & Borun LLP (57) ABSTRACT

The present invention provides a composite sheet material in which a three-dimensional sheet material and a flat sheet material are firmly joined to each other and which is excellent in ventilation and the like, soft, and good in touch. In the composite sheet material, a three-dimensional sheet material having a large number of protruding portions formed thereon and a flat sheet material not having such protruding portions are layered on each other and joined. The three-dimensional sheet material is joined to the flat sheet material at joining parts apart from protruding portions. A plurality of joining parts are formed around each protruding portion in such a manner as to surround the protruding portion. The area of the joining part is less than (Continued)

50% of that of a base surrounded by the protruding portions. Some of the joining parts are provided with a through hole penetrating the composite sheet material.

2 Claims, 8 Drawing Sheets (51) Int. Cl.
| | |
|---|---|
| B32B 3/26 | (2006.01) |
| B32B 3/30 | (2006.01) |
| B32B 5/26 | (2006.01) |
| B32B 5/02 | (2006.01) |
| A61F 13/49 | (2006.01) |
| A61F 13/15 | (2006.01) |
| B32B 37/06 | (2006.01) |
| B32B 37/10 | (2006.01) |
| B32B 37/14 | (2006.01) |
| B32B 38/00 | (2006.01) |

(52) U.S. Cl.
CPC ............ *A61F 13/49* (2013.01); *A61F 13/511* (2013.01); *A61F 13/512* (2013.01); *A61F 13/5116* (2013.01); *B32B 3/266* (2013.01); *B32B 3/30* (2013.01); *B32B 5/022* (2013.01); *B32B 5/26* (2013.01); *B32B 37/06* (2013.01); *B32B 37/10* (2013.01); *B32B 37/14* (2013.01); *B32B 38/0012* (2013.01); *A61F 2013/15715* (2013.01); *B32B 2307/724* (2013.01); *B32B 2307/726* (2013.01); *B32B 2555/02* (2013.01)

(58) Field of Classification Search
CPC ........ A61F 13/512; A61F 5/44; A61F 5/4401; Y10T 428/24322; Y10T 428/24273; Y10T 428/25562; Y10T 428/24661; Y10T 428/24826; B32B 3/266; B32B 3/30; B32B 5/022; B32B 5/26
See application file for complete search history.

(56) References Cited

U.S. PATENT DOCUMENTS

| | | | | |
|---|---|---|---|---|
| 3,837,991 | A * | 9/1974 | Evans | B65D 65/406 428/118 |
| 3,908,052 | A * | 9/1975 | Sanders | C09K 19/544 428/1.5 |
| 4,028,750 | A * | 6/1977 | Gustafsson | E04H 4/10 4/498 |
| 4,055,180 | A * | 10/1977 | Karami | A61F 13/5323 604/368 |
| 4,638,907 | A * | 1/1987 | Bedenk | A47L 13/17 162/109 |
| 4,748,789 | A * | 6/1988 | Hedley | E04F 15/02405 52/783.1 |
| 5,188,625 | A * | 2/1993 | Van Iten | A61F 13/15577 604/383 |
| 5,817,394 | A * | 10/1998 | Alikhan | B29C 65/18 428/137 |
| 6,060,149 | A * | 5/2000 | Nissing | B32B 29/02 428/138 |
| 6,803,334 | B2 * | 10/2004 | Mizutani | A61F 13/512 428/103 |
| 8,180,603 | B2 * | 5/2012 | Blessing | A61F 13/15658 703/2 |
| 2001/0008683 | A1 * | 7/2001 | Takai | A61F 13/42 428/196 |
| 2002/0042600 | A1 * | 4/2002 | Datta | A61F 13/49014 604/385.13 |
| 2002/0058128 | A1 * | 5/2002 | Toyoshima | A61F 13/51108 428/182 |
| 2002/0082576 | A1 * | 6/2002 | Hansson | A61F 13/472 604/381 |
| 2002/0099347 | A1 * | 7/2002 | Chen | A61F 13/512 604/369 |
| 2002/0193774 | A1 * | 12/2002 | Otsubo | A61F 13/51464 604/385.22 |
| 2003/0050615 | A1 * | 3/2003 | Sakamoto | A61F 13/51104 604/358 |
| 2003/0181882 | A1 * | 9/2003 | Toyoshima | A61F 13/51104 604/367 |
| 2004/0140047 | A1 | 7/2004 | Sato et al. | |
| 2005/0203472 | A1 * | 9/2005 | Sakaguchi | A61F 13/49 604/367 |
| 2006/0243367 | A1 * | 11/2006 | Engelhart | A61F 13/15707 156/62.6 |
| 2006/0270302 | A1 | 11/2006 | Ando et al. | |
| 2007/0207293 | A1 * | 9/2007 | Santiago | D21H 27/02 428/174 |
| 2007/0257402 | A1 * | 11/2007 | Rasmussen | B29C 53/28 264/339 |
| 2009/0092797 | A1 | 4/2009 | Sato et al. | |
| 2010/0209664 | A1 * | 8/2010 | Sato | B32B 3/266 428/138 |
| 2010/0233503 | A1 * | 9/2010 | Zachman | B32B 15/01 428/593 |
| 2010/0249740 | A1 | 9/2010 | Miyamoto et al. | |
| 2011/0004176 | A1 * | 1/2011 | Andersson | A61F 13/512 604/378 |
| 2011/0042011 | A1 | 2/2011 | Sato et al. | |
| 2012/0059343 | A1 | 3/2012 | Kume et al. | |
| 2013/0284362 | A1 * | 10/2013 | Tsujimoto | A61F 13/15617 156/276 |

FOREIGN PATENT DOCUMENTS

| | | |
|---|---|---|
| JP | 2009039140 A | 2/2009 |
| JP | 2009050538 A | 3/2009 |
| JP | 2009160035 A | 7/2009 |
| JP | 2012-111076 A | 6/2012 |
| TW | I343801 B | 6/2011 |
| WO | WO-2010119535 A1 | 10/2010 |
| WO | WO-2012108330 A1 * | 8/2012 ....... A61F 13/15617 |

OTHER PUBLICATIONS

International Preliminary Report on Patentability for Application No. PCT/JP2013/080897, dated Jun. 2, 2015. (English Translation).

* cited by examiner

COMPOSITE SHEET MATERIAL, DISPOSABLE WEARING ARTICLE USING THE SAME, AND PRODUCTION METHOD AND PRODUCTION APPARATUS FOR COMPOSITE SHEET MATERIAL

TECHNICAL FIELD

The present invention relates to a composite sheet material used as a surface sheet for disposable wearing articles such as disposable diapers and the like. More specifically, the present invention relates to a composite sheet material in which a three-dimensional sheet material and a flat sheet material are firmly joined to each other and which is excellent in ventilation and the like, soft, and good in touch; a disposable wearing article using the same; and a production method and a production apparatus for said composite sheet material.

BACKGROUND ART

Conventional composite sheet materials used as a surface sheet for a disposable wearing article include one in which a three-dimensional sheet material having a large number of protruding portions formed thereon and a flat sheet material not having such protruding portions are layered on each other (for example, see patent literature 1). A disposable wearing article provided with a surface sheet consisting of this composite sheet material is worn in such a manner that the protruding portions protrude toward the wearer's skin, thereby providing an excellent wearing feeling as well as preventing liquid leakage effectively.

CITATION LIST

Patent Literature

PTL 1: JP 2004-174234 A

SUMMARY OF INVENTION

Technical Problem

The conventional composite sheet material is produced by, with use of a pair of shaping rolls each having, on circumferential surfaces thereof, a large number of recessed and protruding shapes that mesh with each other, passing one sheet material into the meshing part and thereby forming, utilizing the recessions on the roll, protruding portions on the sheet material to give a three-dimensional sheet material;

holding the three-dimensional sheet material on the circumferential surface of one of the rolls by suction and disposing a flat sheet material on the three-dimensional sheet material; and joining the two sheet materials by welding or the like around the recessions on the roll.

Therefore, in the obtained composite sheet material, the whole of the three-dimensional sheet material excluding the parts where protruding portions are formed is joined to the flat sheet material (such a region excluding the protruding portions is hereinafter referred to as "base").

Accordingly, in this conventional composite sheet material, the joining area of the three-dimensional sheet material to the flat sheet material is large, that is, the area in which the sheet materials are in a film-like state or the like due to the welding is also large. Therefore it is not easy to improve the softness of the whole composite sheet material. Moreover, the three-dimensional sheet material, in which the bases adjacent to the protruding portions are joined to the flat sheet material, is excellent in shape holding property and less likely to change its shape when pressed. In view of these points as well, it is not easy to improve the flexibility of the composite sheet material. As a result, it is not easy to further improve the texture and wearing feeling of this composite sheet material used as a surface sheet material.

Due to the largeness of the joining area, applying a higher pressure is not easy, and as a consequence firm joining throughout the adhesion area is not easy. When the three-dimensional sheet material and the flat sheet material are not sufficiently joined and an external force or the like unjoins the sheet materials, there is a risk that the sheet materials may shift with respect to each other and that the three-dimensional shapes of the protruding portions may not be sustained.

Moreover, the turning of the sheet materials into a film-like state as a result of welding, i.e., the turning occurring in large areas each surrounded by the protruding portions, causes a problem of decrease in ventilation and liquid permeability of the composite sheet material as a whole.

In view of the above problems, the present invention is directed to a composite sheet material in which a three-dimensional sheet material and a flat sheet material are firmly joined to each other and which is excellent in ventilation and the like, soft, and good in touch; and a production method and a production apparatus therefor.

Solution to Problem

To solve the above problems, the present invention is constituted as follows, when described referring to FIG. 1 to FIG. 9 showing embodiments of the present invention for example.

Aspect 1 of the present invention relates to a composite sheet material in which a three-dimensional sheet material (2) having a large number of protruding portions (3) formed thereon and a flat sheet material (4) not having such protruding portions are layered on each other and joined, the three-dimensional sheet material (2) being joined to the flat sheet material (4) at joining parts (5) apart from the protruding portions (3).

Aspect 2 of the present invention relates to a disposable wearing article using the composite sheet material (1) according to Aspect 1 of the present invention.

Aspect 3 of the present invention relates to a composite sheet material production method comprising, guiding a first sheet material (17) between a first shaping roll (11) having, on the circumferential surface thereof, recessions for shaping (21) and a second shaping roll (12) having, on the circumferential surface thereof, protrusions for shaping (24) to form a three-dimensional sheet material (2) having a large number of protruding portions (3) formed thereon;

disposing a flat sheet material (4) consisting of a second sheet material (19) on the three-dimensional sheet material (2) ; and pressure-welding the three-dimensional sheet material (2) and the flat sheet material (4) to each other at parts apart from the protruding portions (3) to generate joining parts (5).

Aspect 4 of the present invention relates to a production apparatus for a composite sheet material in which a three-dimensional sheet material (2) having a large number of protruding portions (3) and a flat sheet material (4) not having such protruding portions are layered on each other to be joined, the apparatus comprising a first shaping roll (11), a second shaping roll (12), and pressing rolls (13) disposed parallel to one another in an axial direction, the first shaping roll (11) having, on the circumferential surface thereof, a large number of recessions for shaping (21) and having a shaping position (14) and pressing positions (15, 16) set on the circumferential surface of the roll in this order from the upstream side of the rotation direction, the second shaping roll (12) having, on the circumferential surface thereof, a large number of protrusions for shaping (24), and facing the first shaping roll (11) at the shaping position (14), where the protrusions for shaping (24) mesh with the recessions for shaping (21), either the first shaping roll (11) or the pressing rolls (13) having, on the circumferential surface thereof, projections for pressure-welding (25) protruding outward in a radial direction, the first shaping roll (11) and the pressing rolls (13) facing each other at the pressing positions (15, 16) so that the tips of the projections for pressure-welding (25) press the three-dimensional sheet material (2) and the flat sheet material (4) superposed on each other.

The joining part, which is apart from the protruding portions, accounts for only a part of the base not including the protruding portions, and the joining area is smaller than the whole base. Accordingly, when the three-dimensional sheet material and the flat sheet material are pressure-welded to each other at these joining parts, these sheet materials are firmly joined to each other by high pressure. Moreover, since each joining part is small, the composite sheet material is soft, and since the protruding portions are apart from the joining parts, they easily change their shapes when pressed, exhibiting an excellent flexibility. Moreover, since the joining area is small, even when the joining part is in a film-like state or the like, the composite sheet material as a whole can maintain an excellent ventilation and an excellent liquid permeability. Therefore, a disposable wearing article according to Aspect 2 of the present invention using the composite sheet material as an absorber surface sheet or the like provides a good texture and an excellent wearing feeling.

The composite sheet material is not limited to one produced by a specific production method or a specific production apparatus. However, the composite sheet material is preferably produced by Aspect 3 or 4 of the present invention so that the three-dimensional sheet material and the flat sheet material may be easily and surely joined at predetermined joining parts.

In this case, in the composite sheet material production apparatus of Aspect 4 of the present invention, the above projections for pressure-welding may be provided on the circumferential surface of either the first shaping roll or the pressing rolls. However, it is preferable that the projections for pressure-welding be provided on the circumferential surface of the first shaping roll at positions apart from the recessions for shaping so that the obtained composite sheet material has the joining parts at predetermined relative positions with respect to the protruding portions formed by the recessions for shaping, i.e., at positions apart from the protruding portions.

The joining part has only to be apart from the protruding portions. However, preferably a plurality of joining parts are formed around each protruding portion in such a manner as to surround the protruding portion so that the shape of the protruding portion may be more securely sustained by the surrounding joining parts. Moreover, the joining part is preferably formed in the large part surrounded by adjacent protruding portions, i.e., the part most apart from any of the surrounding protruding portions, so that the three-dimensional sheet material and the flat sheet material may be firmly joined while the shapes of the protruding portions are maintained with an appropriate flexibility. In particular, the joining part is preferably formed only in the large part surrounded by adjacent protruding portions.

Therefore, in the composite sheet material production apparatus of Aspect 4 of the present invention, a plurality of projections for pressure-welding are preferably provided around each recession for shaping in such a manner as to surround the recession preferably in the large part surrounded by adjacent recessions for shaping, i.e., the part most apart from any of the surrounding recessions for shaping.

The area of the joining part is not limited to a specific size. However, when it is too small, there is a risk that the three-dimensional sheet material and the flat sheet material may become unjoined, and when it is too large, sufficient improvement of the flexibility of the composite sheet material cannot be readily achieved. Accordingly, the area of the joining part is preferably less than 50% of that of the base surrounded by the protruding portions, more preferably about 5 to 30% thereof, and still more preferably 10 to 25% thereof. The above "base surrounded by the protruding portions" refers to a region, in a plan view, surrounded by lines each connecting adjacent two central points of the protruding portions neighboring the joining part excluding the parts where the protruding portions are formed. In cases where a plurality of joining parts are formed in the base surrounded by the protruding portions, the above "area of the joining part" refers to the total of the areas of all the joining parts.

The three-dimensional sheet material and the flat sheet material have only to be joined at the joining parts at the time of pressure-welding and may be joined using an adhesive or the like. However, they are preferably joined by heat-welding at the time of pressure-welding without using an adhesive because, in this case, the disuse of any adhesive or the like leads to reduced cost and moreover prevents the composite sheet material from becoming stiff.

Therefore, in the composite sheet material production apparatus of Aspect 4 of the present invention, preferably at least either the first shaping roll or the pressing roll comprises a heating means for heating the three-dimensional sheet material and the flat sheet material, which are pressed by the projections for pressure-welding, so that both the sheet materials may be welded to each other at the time of pressure-welding.

In this case, in the composite sheet material production apparatus, it is preferable that a plurality of pressing rolls be provided around the first shaping roll so that each joining part may be pressure-welded several times and thereby firmly pressure-welded even when the improvement of a production rate and the like has shortened the pressure-welding time at each pressing position. Moreover, such a plurality of pressing rolls can equally pressure-weld the multiple joining parts formed in the large area.

In the above case, it is preferable that the projections for pressure-welding be provided on the circumferential surface of the first shaping roll so that the three-dimensional sheet material and the flat sheet material may be conveyed along with the circumferential surface of the first shaping roll without causing positional displacement with respect to the projections for pressure-welding and thereby each joining part may be surely pressed several times by the projections for pressure-welding and the plurality of pressing rolls without causing positional displacement.

Even when the joining part is in a film-like state as a result of heat-welding, since the area of the joining part is small, an excellent ventilation and an excellent liquid permeability can be achieved. Further, in such case, preferably at least some joining parts are provided with a through hole penetrating the composite sheet material so that the three-dimensional sheet material and the flat sheet material may be firmly joined around the through hole and that the composite sheet material may exhibit a more excellent ventilation and a more excellent liquid permeability due to the through hole. The through holes may be formed by increased pressure in the pressure-welding, a small protrusion formed at the tip of the projection for pressure-welding, or tension applied to the composite sheet material after the welding.

Advantageous Effects of Invention

Constituted and functioning as described above, the present invention produces the following effects.
(1) Since the joining parts are apart from the protruding portions and the area of the joining part is smaller than that of the base surrounded by the protruding portions, the three-dimensional sheet material and the flat sheet material can be firmly joined to each other at these joining parts by high pressure. As a result, the three-dimensional sheet material and the flat sheet material are not at risk of becoming unjoined at the joining parts and thereby shifting with respect to each other, and therefore excessive changes or disappearance of the three-dimensional shapes of the protruding portions due to the shift can be prevented.
(2) Since the area of the joining part is small, the stiffness of the composite sheet material caused by the joining can be reduced. Further, since the joining parts are apart from the protruding portions, each protruding portion easily changes its shape when pressed and the composite sheet material as a whole can exhibit an excellent flexibility. As a result, a disposable wearing article using this composite sheet material as an absorber surface sheet or the like provides a good texture and an excellent wearing feeling.
(3) Since the area of the joining part is small, even when the three-dimensional sheet material and the flat sheet material are firmly joined to each other and these joining parts are in a film-like state or the like, the composite sheet material as a whole can maintain an excellent ventilation and an excellent liquid permeability.

DESCRIPTION OF EMBODIMENTS

The present invention will be concretely described below, referring to the drawings. However, the present invention is not limited to the embodiment described below.

As shown in FIG. 1 to FIG. 4, the composite sheet material (1) comprises a three-dimensional sheet material (2) having a large number of protruding portions (3) and a flat sheet material (4) not having such protruding portions, which is layered on the three-dimensional sheet material (2). The three-dimensional sheet material (2) and the flat sheet material (4) are joined to each other by welding at joining parts (5) formed at positions apart from the protruding portions (3) and are integrated with each other.

The materials of the three-dimensional sheet material (2) and flat sheet material (4) are not limited to specific ones. For example, nonwoven fabrics produced by various processes, such as an air through nonwoven fabric, a spun lace nonwoven fabric, a spunbonded nonwoven fabric, and a melt-blown nonwoven fabric, are used. The three-dimensional sheet material (2) and the flat sheet material (4) may be the same or different from each other in material.

Figure 1:
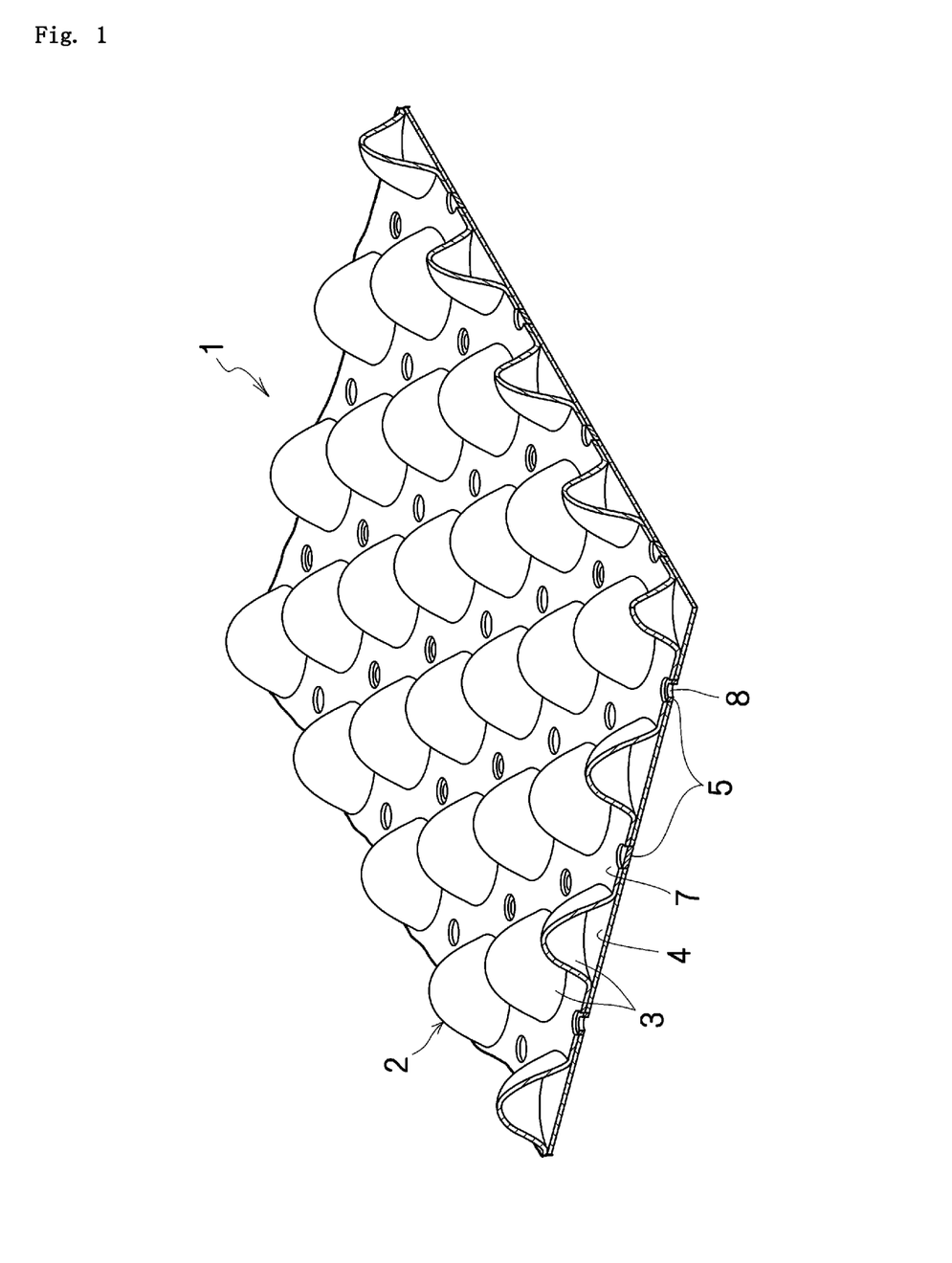
FIG. 1 is a broken perspective view of a composite sheet material, showing an embodiment of the present invention.
Figure 2:
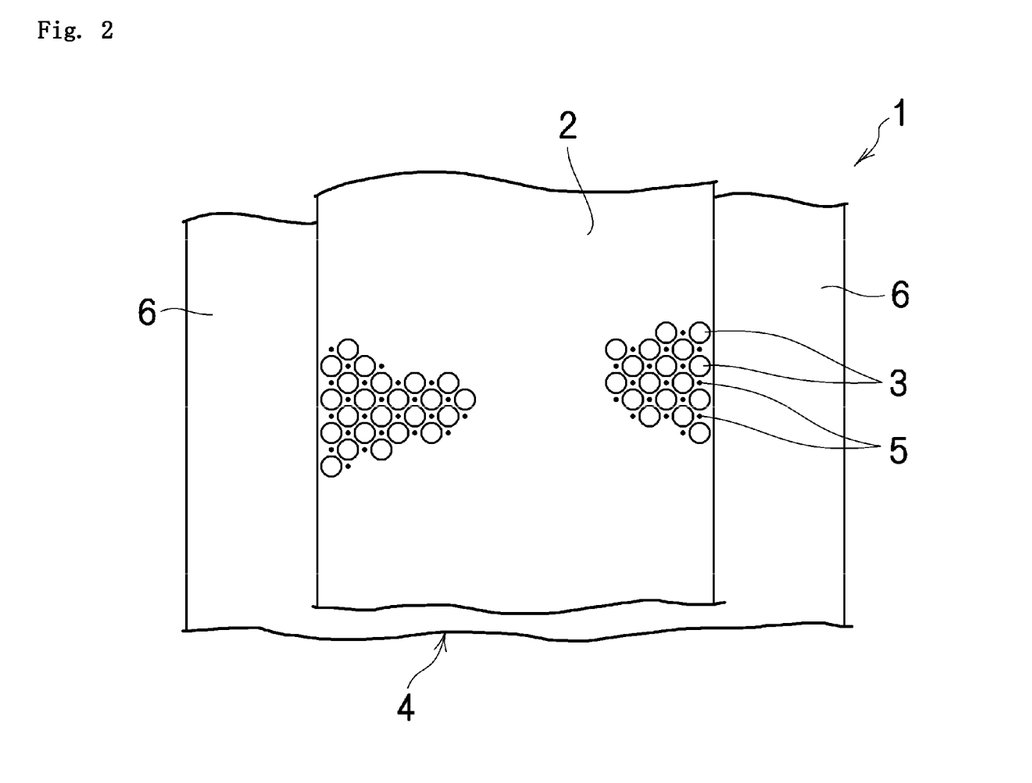
FIG. 2 is a plan view of the composite sheet material according to the embodiment of the present invention.

As shown in FIG. 2, in this embodiment, the flat sheet material (4) is formed with a width greater than that of the three-dimensional sheet material (2), and a large number of protruding portions (3) are formed over the whole width of the narrower three-dimensional sheet material (2). Therefore, the composite sheet material (1) has, along both side edges, flat areas (6) not having protruding portions formed. The flat areas (6) are formed only of the flat sheet material (4), well maintaining the softness of the whole composite sheet material (1).

Figure 5:
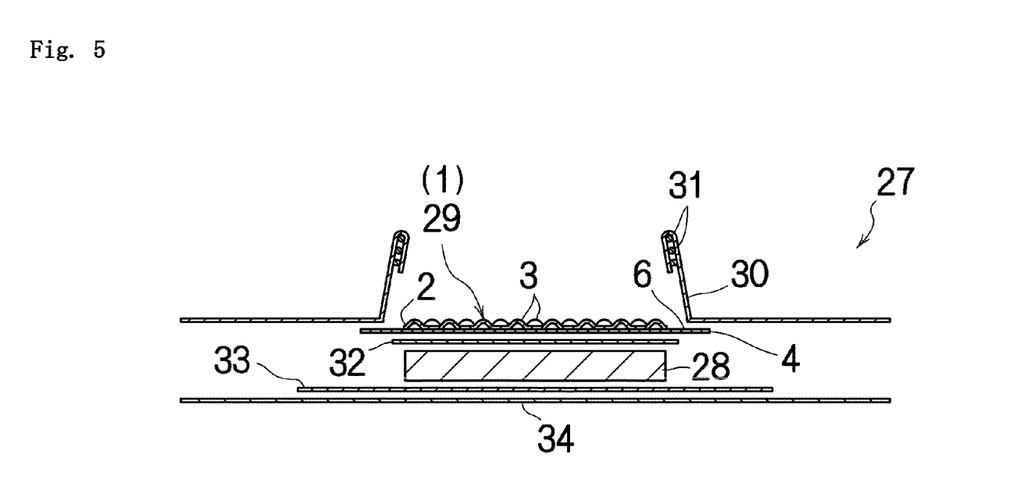
FIG. 5 is an exploded cross-section view, showing a schematic configuration of a disposable wearing article according to the embodiment of the present invention.

As shown in FIG. 5, for example, in cases where the composite sheet material (1) is used as a surface sheet (29) for an absorber (28) of a disposable diaper (27), advantageously the flat area (6) can be easily joined to another sheet such as a three-dimensional gather sheet (30). The flat area (6) may also be bent and used in such a manner as to wrap both side edges of the absorber (28). Reference numeral (31) indicates a threadlike elastic member attached to the three-dimensional gather sheet (30), reference numeral (32) indicates a diffusion sheet, reference numeral (33) indicates a back seat, and reference numeral (34) indicates an outer layer sheet.

In the present invention, the widths of the three-dimensional sheet material (2) and flat sheet material (4) are not limited to specific ones. The width of the three-dimensional sheet material (2) may be the same as or greater than that of the flat sheet material (4). The protruding portions (3) are formed across the same width as that of the narrower sheet material or in an area having a further narrower width.

Figure 3:
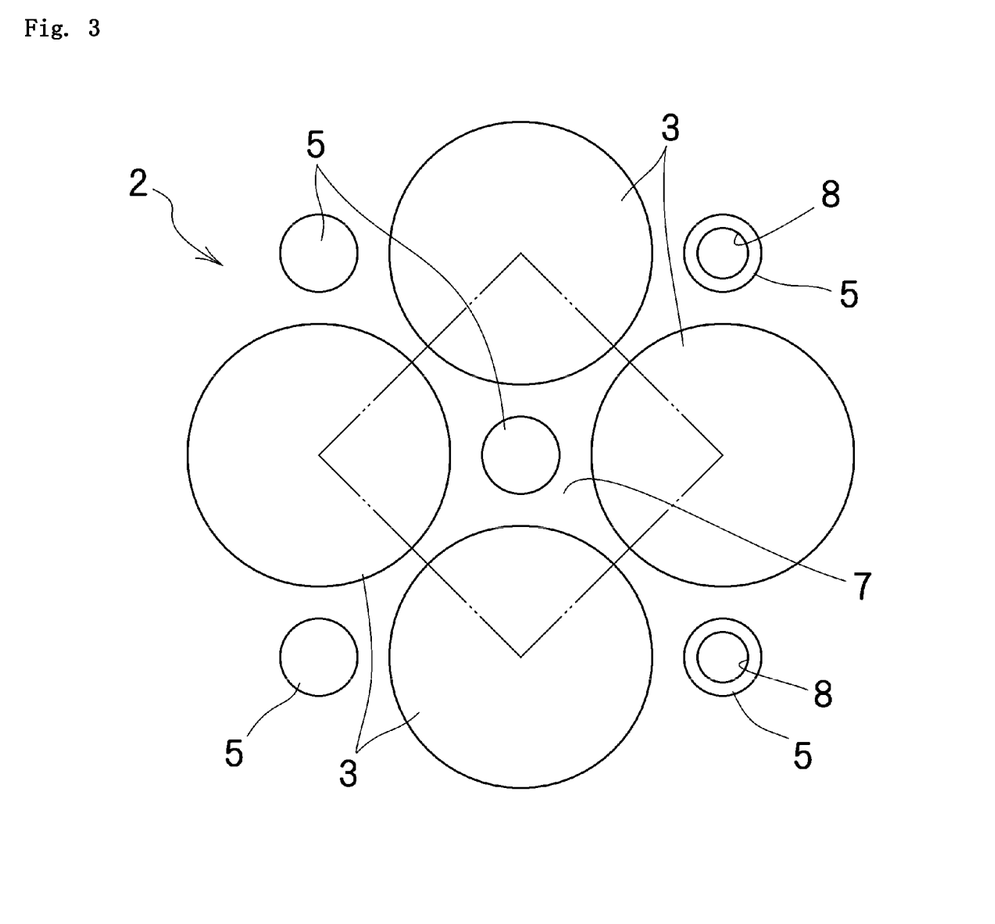
FIG. 3 is an enlarged plan view of the main part of the composite sheet material according to the embodiment of the present invention.

As shown in FIG. 2 and FIG. 3, four joining parts (5) are formed around each protruding portion (3) in such a manner as to surround the protruding portion (3). The joining part (5) is formed in the large part surrounded by adjacent protruding portions (3), i.e., the part most apart from any of the surrounding protruding portions (3). That is, in this embodiment, each protruding portion (3) is arranged in such a manner that the center of the protruding portion (3) may be situated at each apex of a quadrangle in a plan view and the joining part (5) is formed at the center of the quadrangle.

The dimensions of the protruding portion (3) and joining part (5) are not limited to specific ones. However, for example, the protruding portion (3) is preferably equivalent to a true circle with a diameter of about 0.5 to 10 mm and the joining part (5) is preferably equivalent to a true circle with a diameter of about 0.1 to 2 mm.

Moreover, the area of the joining part (5) is preferably less than 50% of that of the base (7) surrounded by the protruding portions (3). For example, in FIG. 3, the area of the joining part (5) is set to, for example, about 20% with respect to the area of the above quadrangle excluding the parts where the protruding portions (3) are formed (i.e., base).

Figure 4:
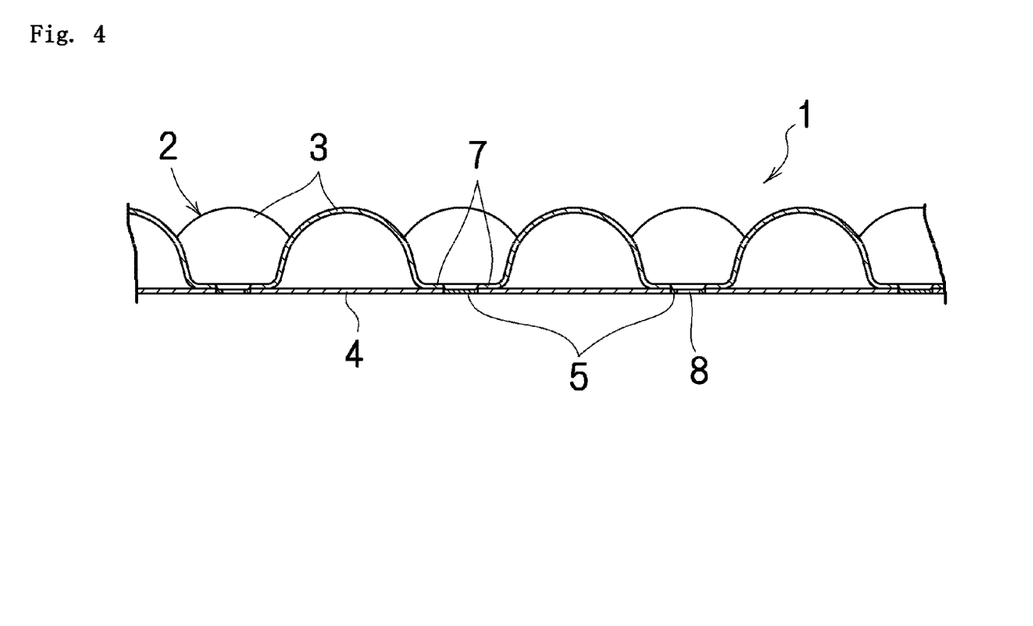
FIG. 4 is an enlarged cross-section view of the main part of the composite sheet material according to the embodiment of the present invention.

As shown in FIG. 4, a through hole (8) penetrating the composite sheet material (1) is formed in some of the joining parts (5) to improve the ventilation and liquid permeability of the whole composite sheet material (1). In the present invention, however, when the ventilation and liquid permeability of the three-dimensional sheet material (2) and flat sheet material (4) are high enough, the through hole (8) may be omitted. Alternatively, to further improve the ventilation and the liquid permeability, the through hole (8) may also be formed in every joining part.

Next, an apparatus for producing the composite sheet material and a production method using said production apparatus will be described.

Figure 6:
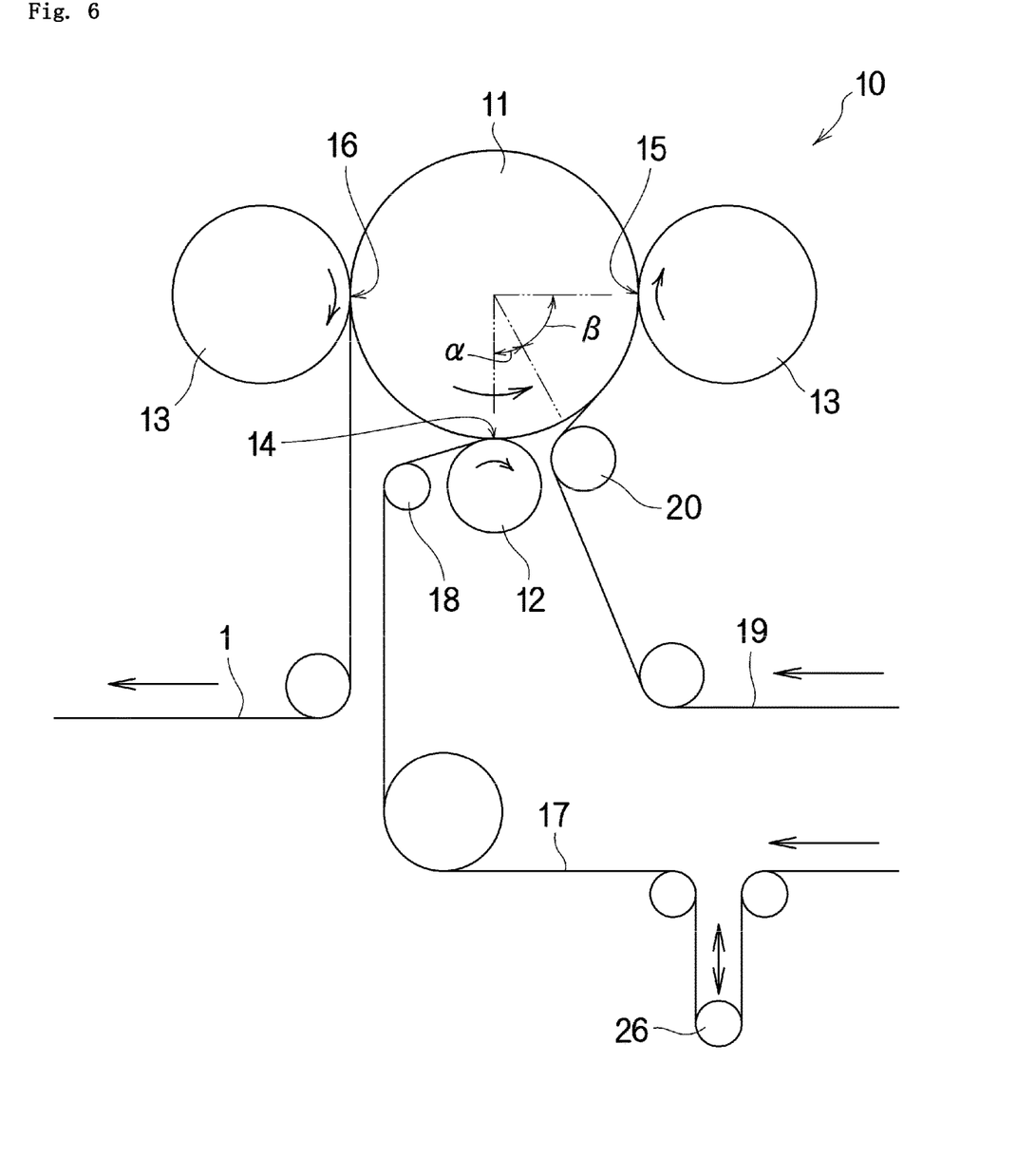
FIG. 6 is a schematic configuration view of a composite sheet material production apparatus according to the embodiment of the present invention.

As shown in FIG. 6, a production apparatus (10) of this composite sheet material comprises a first shaping roll (11), a second shaping roll (12), and two pressing rolls (13, 13) disposed parallel to one another in the axial direction.

On the circumferential surface of the first shaping roll (11), a shaping position (14), a first pressing position (15), and a second pressing position (16) are set in order from the upstream side of the rotation direction. The second shaping roll (12) faces the first shaping roll (11) at the shaping position (14) and the pressing rolls (13, 13) face the first shaping roll (11) at the first pressing position (15) and the second pressing position (16), respectively.

The production apparatus (10) further comprises a first supply means (18) and a second supply means (20). The first supply means (18) supplies a first sheet material (17) from a supply device not shown in the figure to the upstream side of the shaping position (14) via a tension controller (26). The second supply means (20) supplies a second sheet material (19) from a supply device not shown in the figure to a position between the shaping position (14) and the first pressing position (15). The supply means (18, 20) are provided with a preheating means not shown in the figure for preheating the sheet materials (17, 19) supplied by the supply means, respectively.

Figure 7:
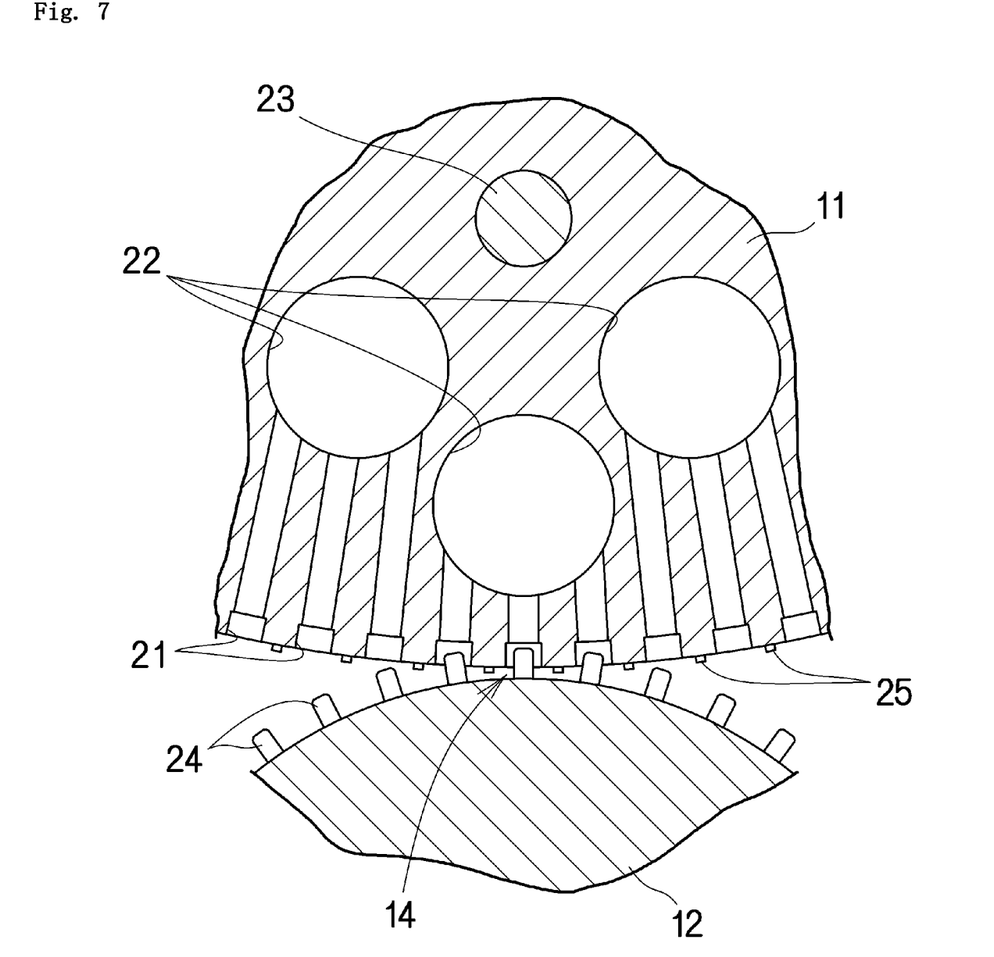
FIG. 7 is an enlarged cross-section view of the main part of the composite sheet material production apparatus according to the embodiment of the present invention.

As shown in FIG. 7, a large number of recessions for shaping (21) are formed on the circumferential surface of the first shaping roll (11). A suction means not shown in the figure is connected to the bottoms of the recessions for shaping (21) via suction paths (22) formed in the first shaping roll (11). Moreover, in the first shaping roll (11), a heating means (23) is provided for heating the first sheet material (17) and the second sheet material (19) which are conveyed along with the circumferential surface of the roll.

The second shaping roll (12) is provided with a large number of protrusions for shaping (24) on the circumferential surface thereof. The protrusions for shaping (24) mesh with the recessions for shaping (21) at the shaping position (14). In the second shaping roll (12), a preheating means not shown in the figure is provided. The preheating means prevents the first sheet material (17) passing through between the shaping rolls (11, 12) from being cooled due to the contact with the second shaping roll (12).

The circumferential surface of the first shaping roll (11) has projections for pressure-welding (25) protruding outward in a radial direction, each of which is situated in the part surrounded by adjacent recessions for shaping (21) so as to be apart from the recessions for shaping (21). The positions of the projections for pressure-welding (25) correspond to joining parts (5) to be formed in the composite sheet material (1). Therefore, four projections for pressure-welding (25) are provided around each recession for shaping (21) in such a manner as to surround the recession for shaping (21). Each projection for pressure-welding (25) is provided in the large part surrounded by adjacent recessions for shaping (21), i.e., the part most apart from any of the surrounding recessions for shaping (21).

The tips of the projections for pressure-welding (25) press the three-dimensional sheet material (2) and the flat sheet material (4), which are superposed on each other, against the pressing rolls (13, 13) at the pressing positions (15, 16), respectively. Therefore, the projection for pressure-welding (25) has only to be high enough to press the sheet materials (2, 4) and is formed to have a protrusion height as slight as, for example, 1 mm or less.

Moreover, in each pressing roll (13), a heating means not shown in the figure is provided for thermocompression bonding of the three-dimensional sheet material (2) and the flat sheet material (4) pressed by the projections for pressure-welding (25).

As shown in FIG. 6, the first sheet material (17) is supplied from a supply device not shown in the figure via the first supply means (18). When passed between the first shaping roll (11) and the second shaping roll (12) at the shaping position (14), the first sheet material (17) is partly pushed by the protrusions for shaping (24) into the recessions for shaping (21), and thus a large number of protruding portions (3) are formed. At this time, the tension of the first sheet material (17) is adjusted using the tension controller (26) so as to be uniform over the entire sheet material, and thereby the protruding portions (3) are uniformly formed.

The recessions for shaping (21) and the protrusions for shaping (24) are formed, throughout an area with the same width as that of the first sheet material (17) on the circumferential surfaces of the first shaping roll (11) and the second shaping roll (12) and thereby a large number of protruding portions (3) are formed over the whole width of the three-dimensional sheet material (2).

The recession for shaping (21) is formed to have a depth greater than the value obtained by subtracting the height of the projection for pressure-welding (25) from the height of the protrusion for shaping (24). Accordingly, even when the projections for pressure-welding (25) are provided on the circumferential surface of the first shaping roll (11), the portions of the first sheet material (17) pushed by the protrusions for shaping (24) are surely received in the recessions for shaping (21). The peripheral edge of the end of the protrusion for shaping (24) is chamfered to a curved surface so that the first sheet material (17) pushed into the recessions for shaping (21) may not get damaged.

Since the first sheet material (17) is heated by the heating means (23) provided in the first shaping roll (11) and the preheating means provided in the second shaping roll (12) and the first supply means (18), the portions of the first sheet material (17) pushed into the recessions for shaping (21) are easily and surely shaped into the protruding portions (3), and thus the three-dimensional sheet material (2) is produced.

The three-dimensional sheet material (2) having the protruding portions (3) shaped thereon is sucked by the suction means via the suction paths (22) and thereby held on the circumferential surface of the first shaping roll (11). Therefore, the protruding portions (3) are prevented from coming off the recessions for shaping (21) and the three-dimensional sheet material (2) is smoothly guided to the first pressing position (15) and then the second pressing position (16).

Meanwhile, the second sheet material (19) is supplied from a supply device not shown in the figure, via the second supply means (20), to a position between the shaping position (14) and the first pressing position (15). Here, the second sheet material (19) is superposed, as the flat sheet material (4), on the three-dimensional sheet material (2).

At this time, the second sheet material (19) is supplied via the second supply means (20) to a position as close as possible to the shaping position (14) rather than the first pressing position (15). That is, as shown in FIG. 6, the arrangement position of the second supply means (20) relative to the first shaping roll (11) is set in such a manner that the central angle ($\alpha$) between the arrangement position and the shaping position (14) may be smaller than the central angle ($\beta$) between the arrangement position and the first pressing position (15). Accordingly, the recessions for shaping (21) are covered with the flat sheet material (4) early and therefore the negative pressure in the suction paths (22) can be favorably ensured. The flat sheet material (4) and the three-dimensional sheet material (2) are firmly held on the circumferential surface of the first shaping roll (11) and guided to the first pressing position (15).

The second sheet material (19) is heated by the preheating means provided in the second supply means (20) and therefore there is no risk that the three-dimensional sheet material (2) may be cooled even when the flat sheet material (4) consisting of the second sheet material (19) is superposed on the three-dimensional sheet material (2). As a result, the three-dimensional sheet material (2) and the flat sheet material (4) are guided in a heated state to the first pressing position (15).

When the three-dimensional sheet material (2) and the flat sheet material (4), which are superposed on each other, reach the first pressing position (15), parts apart from the protruding portions (3) of the sheet materials (2, 4) are pressed by the tips of the projections for pressure-welding (25). The pressing force is received by the pressing roll (13), and the sheet materials (2, 4) are pressure-welded. Then, the sheet materials (2, 4) are further guided to the second pressing position (16) and similarly pressure-welded by the tips of the projections for pressure-welding (25) at the second pressing position (16). Since each pressing roll (13) is sufficiently heated, the sheet materials (2, 4) are welded to each other at the parts pressure-welded. Accordingly, joining parts (5) are formed to give a composite sheet material (1) in which the sheet materials (2, 4) are joined to each other at the joining parts (5). After passing through the second pressing position (16), the composite sheet material (1) comes off the circumferential surface of the first shaping roll (11) and is sent to the next step.

The composite sheet material and the production method and the production apparatus therefor described above are only exemplary embodiments of the technical idea of the present invention. The material, dimension, shape, structure, disposition, and the like of each part are not limited to those described in the embodiment, and various changes can be made within the scope of claims of the present invention.

For example, in the embodiment described above, each protruding portion (3) formed in the three-dimensional sheet material (2) is arranged in such a manner that the center of the protruding portion (3) may be situated at each apex of a quadrangle in a plan view. However, in the present invention, the protruding portion may be arranged in any pattern and may be arranged, for example, in such a manner that the center of the protruding portion may be situated at each apex of a triangle in a plan view. In this case, the joining part is preferably formed in the center of the triangle.

In the embodiment described above, one joining part (5) is formed in the base (7) surrounded by the protruding portions (3).

Figure 8:
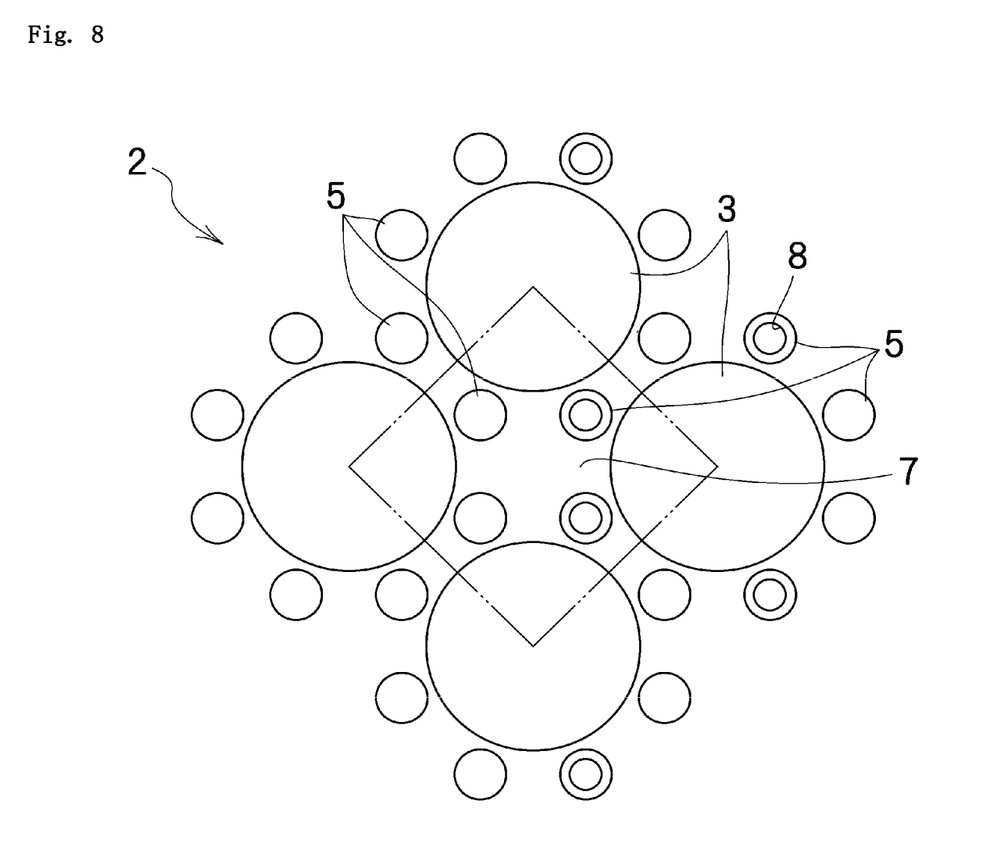
FIG. 8 is an enlarged plan view of the main part of the composite sheet material according to Variation 1 of the present invention.
Figure 9:
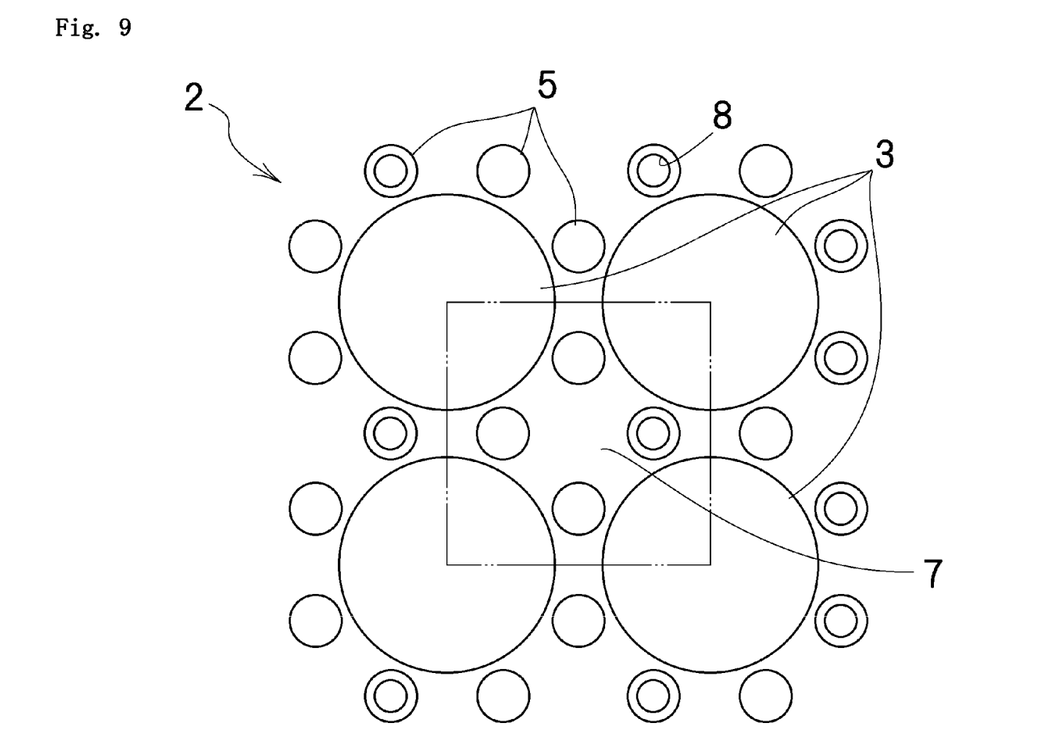
FIG. 9 is an enlarged plan view of the main part of the composite sheet material according to Variation 2 of the present invention.

However, in the present invention, a plurality of joining parts (5) may be provided in the base (7) surrounded by the protruding portions (3), for example, as in Variation 1 shown in FIG. 8. In Variation 1, eight joining parts (5) are formed around each protruding portion (3) and therefore advantageously the shape of each protruding portion (3) can be well sustained.

In the embodiment and Variation 1 described above, the protruding portions (3) are arranged in such a manner as to be aligned in a direction oblique to the length direction of the three-dimensional sheet material (2). However, in the present invention, the protruding portions (3) may be arranged in such a manner as to be aligned in the length direction and width direction of the three-dimensional sheet material (2), for example, as in Variation 2 shown in FIG. 9.

In the embodiment and each Variation described above, the protruding portion and the joining part are preferably formed into a circle in a plan view so that the recessions for shaping, the projections for pressure-welding, and the like may be easily produced. However, in the present invention, the shapes of the protruding portion and the joining part are not limited to specific shapes, and may be formed into any shape such as a polygon, an ellipse, or a star.

Moreover, in the embodiment described above, it is preferable that the projections for pressure-welding be provided on the circumferential surface of the first shaping roll so that the joining parts formed by the projections for pressure-welding may be easily formed at predetermined relative positions with respect to the protruding portions formed by the recessions for shaping. However, in the present invention, the projections for pressure-welding may be provided on the circumferential surface of the pressing roll.

In the embodiment described above, only the protrusions for shaping are provided on the circumferential surface of the second shaping roll. However, in the present invention, on the circumferential surface of the second shaping roll, small recessions which mesh with the projections for pressure-welding may be formed. In this case, the recession for shaping is preferably formed to have a depth greater than the height of the protrusion for shaping.

In the embodiment described above, each of the first shaping roll and the two pressing rolls is provided with a heating means, and each of the second shaping roll and the two supply means is provided with a preheating means. However, in the present invention, in cases where the three-dimensional sheet material and the flat sheet material are welded to each other at the joining parts, a heating means has only to be provided in at least any of the first shaping roll and the pressing rolls, and other heating means and preheating means can be omitted.

In the embodiment described above, the three-dimensional sheet material and the flat sheet material are welded to each other at the joining parts. However, in the present invention, the three-dimensional sheet material and the flat sheet material may be bonded to each other with an adhesive or the like at the joining parts. In this case, the heating means can be omitted.

Needless to say, the material and width of each sheet material, the size, height, and cross-sectional shape of the protruding portion, the size of the joining part, and the like are not limited to those described in the embodiment.

INDUSTRIAL APPLICABILITY

The composite sheet material of the present invention, in which a three-dimensional sheet material and a flat sheet material are firmly joined to each other, is excellent in ventilation and the like, soft, and good in touch, and useful as, in particular, a surface sheet for disposable wearing articles such as disposable diapers and sanitary napkins. The composite sheet material of the present invention is also useful as composite sheet materials for other purposes, such as outer layer sheets of disposable diapers.

REFERENCE SIGNS LIST 1. composite sheet material
2. three-dimensional sheet material
3. protruding portions
4. flat sheet material
5. joining parts
6. flat areas
7. base
8. through holes
10. composite sheet material production apparatus
11. first shaping roll
12. second shaping roll
13. pressing roll
14. shaping position
15. first pressing position
16. second pressing position
17. first sheet material
18. first supply means
19. second sheet material
20. second supply means
21. recessions for shaping
22. suction path
23. heating means
24. protrusions for shaping
25. projections for pressure-welding
26. tension controller
27. disposable wearing article (disposable diaper)
28. absorber
29. surface sheet
30. three-dimensional gather sheet
31. threadlike elastic member
32. diffusion sheet
33. back seat
34. outer layer sheet α. central angle between arrangement position of second supply means (20) and shaping position (14) in first shaping roll (11)

β. central angle between arrangement position of second supply means (20) and first pressing position (15) in first shaping roll (11)

The invention claimed is:

1. A composite sheet material comprising:
    a three-dimensional sheet material consisting of a nonwoven fabric having a multiplicity of protruding portions formed thereon and
    a flat sheet material consisting of a nonwoven fabric not having such protruding portions,
    which are layered on each other and joined to each other by welding at joining parts,
    a base of the three-dimensional sheet material not including the protruding portions being flat,
    the base being in planar-contact with the flat sheet, and
    the three-dimensional sheet material being joined to the flat sheet material at the joining parts at the base,
    wherein the area of the joining parts is 10 to 25% of the whole of the three-dimensional sheet material excluding the parts where protruding portions are formed, and some of the joining parts are provided with a through hole penetrating the composite sheet material, a plurality of joining parts is formed around each protruding portion in such a manner as to surround each protruding portion, and the joining parts are spaced apart from any adjacent protruding portion, and the protruding portions are hollow.

2. A disposable wearing article comprising a composite sheet material according to claim 1.

* * * * *